United States Patent [19]

Eidenschink et al.

[11] 4,415,470
[45] Nov. 15, 1983

[54] LIQUID CRYSTALLINE FLUORINE-CONTAINING CYCLOHEXYLBIPHENYLS AND DIELECTRICS AND ELECTRO-OPTICAL DISPLAY ELEMENTS BASED THEREON

[75] Inventors: Rudolf Eidenschink, Dieburg; Ludwig Pohl, Darmstadt, both of Fed. Rep. of Germany

[73] Assignee: Merck Patent Gesellschaft mit beschränkter Haftung, Darmstadt, Fed. Rep. of Germany

[21] Appl. No.: 320,146

[22] Filed: Nov. 10, 1981

[30] Foreign Application Priority Data

Nov. 10, 1980 [DE] Fed. Rep. of Germany ....... 3042391

[51] Int. Cl.³ .................. C09K 3/34; G02F 1/133; C07C 121/64; C07C 25/18; C07C 43/225
[52] U.S. Cl. .................. 252/299.63; 252/299.5; 260/465 C; 260/465 F; 260/465 G; 350/350 R; 570/129; 568/642; 568/647
[58] Field of Search .......... 252/299.5, 299.63; 350/350 R; 570/129; 260/465 C, 465 F, 465 G; 568/642, 647

[56] References Cited

U.S. PATENT DOCUMENTS

| | | | |
|---|---|---|---|
| 4,130,502 | 12/1978 | Eidenschink et al. | 252/299.63 |
| 4,154,697 | 5/1979 | Eidenschink et al. | 252/299.63 |
| 4,181,625 | 1/1980 | Eidenschink et al. | 252/299.63 |
| 4,211,666 | 7/1980 | Inukai et al. | 252/299.6 |
| 4,302,352 | 11/1981 | Eidenschink et al. | 252/299.63 |
| 4,330,426 | 5/1982 | Eidenschink et al. | 252/299.5 |
| 4,331,552 | 5/1982 | Eidenschink et al. | 252/299.5 |
| 4,340,498 | 7/1982 | Sugimori | 252/299.5 |
| 4,368,135 | 1/1983 | Osman | 252/299.63 |

FOREIGN PATENT DOCUMENTS

| | | | |
|---|---|---|---|
| 19665 | 12/1980 | European Pat. Off. | 252/299.63 |
| 62470 | 10/1982 | European Pat. Off. | 252/299.63 |
| 2933563 | 2/1981 | Fed. Rep. of Germany | 252/299.63 |
| 2939782 | 4/1981 | Fed. Rep. of Germany | 252/299.64 |
| 2949080 | 6/1981 | Fed. Rep. of Germany | 252/299.62 |
| 3006666 | 9/1981 | Fed. Rep. of Germany | 252/299.63 |
| 3139130 | 5/1982 | Fed. Rep. of Germany | 252/299.63 |
| 53-82676 | 7/1978 | Japan | 252/299.5 |
| 53-82679 | 7/1978 | Japan | 252/299.68 |
| 54-148184 | 11/1979 | Japan | 252/299.63 |
| 57-40429 | 3/1982 | Japan | 252/299.66 |
| 57-159730 | 10/1982 | Japan | 252/299.63 |
| 57-165326 | 10/1982 | Japan | 252/299.63 |
| 2039937 | 8/1980 | United Kingdom | 252/299.66 |
| 2078727 | 1/1982 | United Kingdom | 252/299.63 |
| 2086385 | 5/1982 | United Kingdom | 252/299.6 |

OTHER PUBLICATIONS

Gray, C. W., Mol. Cryst. Liq. Cryst., vol. 63, pp. 3–18, (1981).
Gray, C. W., et al., Mol. Cryst. Liq. Cryst., vol. 67, pp. 1–24, (1981).
Gray, C. W., et al., Mol. Cryst. Liq. Cryst., vol. 53, pp. 147–166, (1979).

Primary Examiner—Teddy S. Gron
Attorney, Agent, or Firm—Millen & White

[57] ABSTRACT

A Cyclohexylbiphenyl of the formula

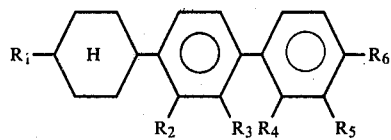

wherein
$R_1$ is alkyl of 1–12 C atoms;
$R_6$ is alkyl or alkoxy each of 1–12 C atoms, CN or fluorine; and
$R_2$, $R_3$, $R_4$ and $R_5$ each is hydrogen or fluorine, with the proviso that at least one, but not more than two of $R_2$, $R_3$, $R_4$, $R_5$ and $R_6$ are fluorine.

8 Claims, No Drawings

LIQUID CRYSTALLINE FLUORINE-CONTAINING CYCLOHEXYLBIPHENYLS AND DIELECTRICS AND ELECTRO-OPTICAL DISPLAY ELEMENTS BASED THEREON

BACKGROUND OF THE INVENTION

The characteristics whereby nematic or nematiccholesteric liquid-crystalline materials significantly vary their optical properties, such as light absorption, light scattering, birefringence, reflectivity or color, under the influence of electric fields, are widely utilized for electro-optical display elements. The functioning of display elements of this type is based, for example, on the phenomena of dynamic scattering, the deformation of aligned phases, the Schadt-Helfrich effect in the twisted cell or the cholesteric-nematic phase transition.

For the technical application of these effects in electronic components, liquid-crystalline dielectrics are required which must meet a large number of demands. Chemical resistance to moisture, air and physical influences, such as heat, infrared, visible and ultraviolet radiation, and continuous and alternating electric fields, is of particular importance. Industrially usable liquid-crystalline dielectrics are also required to have a liquid-crystalline mesophase in the temperature range from at least $+10°$ C. to $+50°$ C., preferably from $0°$ C. to $60°$ C., and the lowest possible viscosity at room temperature, which preferably should not exceed $70 \times 10^{-3}$ Pa.s. Finally, they must not have any characteristic absorption in the visible region, that is, they must be colorless.

A number of liquid-crystalline compounds has already been disclosed, which fulfill the stability demands made on dielectrics intended for electronic components, and which are also colorless. These include, in particular, the p,p'-disubstituted phenyl benzoates described in German Offenlegungsschrift No. 2,139,628 and the p,p'-disubstituted phenylcyclohexane derivatives described in German Offenlegungsschrift No. 2,636,684. In both these classes of compounds, and also in other known series of compounds with a liquid-crystalline mesophase, there are no individual compounds which form a liquid-crystalline nematic mesophase in the required temperature range from $10°$ C. to $60°$ C. As a rule, mixtures of two or more compounds are therefore prepared in order to obtain substances which can be used as liquid-crystalline dielectrics. For this purpose, at least one compound having a low melting point and clear point is usually mixed with another compound having a markedly higher melting point and clear point. This normally gives a mixture, the melting point of which is below that of the lower-melting component, while the clear point is between the clear points of the components. Nevertheless, difficulties arise again and again in the preparation of optimum dielectrics, because the components having the high melting points of clear points frequently also impart a high viscosity to the mixtures. As a result, the switching times of the electro-optical display elements produced with these mixtures, are extended in an undesirable manner. Moreover, problems are frequently caused by the fact that the mutual solubility of the various components, in particular at room temperature or lower temperatures, is only very limited.

SUMMARY OF THE INVENTION

Accordingly, it is an object of the present invention to prepare liquid crystalline dielectrics which have a nematic phase within the required temperature range and, which when used in liquid crystal cells, make possible switching times which are sufficiently short at and below room temperature.

Upon further study of the specification and appended claims, further objects and advantages of this invention will become apparent to those skilled in the art.

These objects have been achieved by providing cyclohexylbiphenyl derivatives of formula (I)

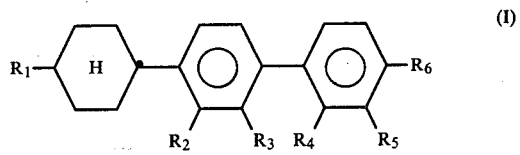

wherein $R_1$ is alkyl of 1–12 C atoms, $R_6$ is alkyl or alkoxy each of 1–12 atoms, CN or fluorine, and $R_2$, $R_3$, $R_4$ and $R_5$ are hydrogen or fluorine, with the proviso that at least one, but not more than two of $R_2$, $R_3$, $R_4$, $R_5$ and $R_6$ are fluorine.

These are outstandingly suitable for use as components of liquid-crsytalline dielectrics. Additionally, these compounds have an extremely wide range of application.

DETAILED DISCUSSION

Depending on the selection of the substituents, the compounds of formula (I) can be used as base materials representing the predominant part of liquid-crystalline dielectrics, or they can be added in smaller proportions of, for example, 2 to 45 percent by weight, to liquidcrystalline base materials from other classes of compounds, in order to prepare dielectrics having a widened liquid-crystalline mesophase or to influence the magnitude of the dielectric anisotropy of such a dielectric.

By a suitable selection of the substituents $R_1$ to $R_6$, the compounds of formula (I) can be used, e.g., for the preparation of dielectrics having a pronounced positive dielectric anistropy, e.g., for use in display elements based on the twisted nematic cell or on the cholesteric-nematic phase transition; or it is also possible to prepare dielectrics having a dielectric anisotropy which only slightly differs from zero or is even negative, these dielectrics being used, e.g., in display elements based on dynamic scattering or on the deformation of aligned phases (DAP effect).

In the pure state, the compounds of formula (I) are colorless, and they form nematic mesophases of low viscosity in a temperature range which is astonishingly wide and is favorable for electro-optical applications.

The invention, thus, relates to cyclohexylbiphenyl derivatives of formula (I) and to their use as components of liquid-crystalline dielectrics. Moreover, the invention relates to liquid-crystalline dielectrics containing at least one cyclohexylbiphenyl derivative of formula (I), and to electro-optical display elements based on a liquid crystal cell, which contain a liquid-crystalline dielectric of this type.

The cyclohexylbiphenyl derivatives of this invention comprise, in particular, the 4-(trans-4-alkylcyclohexyl)-4'-fluorobiphenyls of formula (Ia),

the 4-(trans-4-alkylcyclohexyl)-3'-fluoro-4'-($R_7$)-biphenyls of formula (Ib),

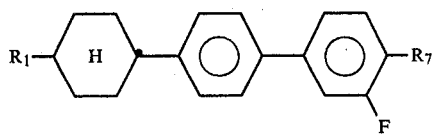

the 4-(trans-4-alkylcyclohexyl)-3',4'-difluorobiphenyls of formula (Ic),

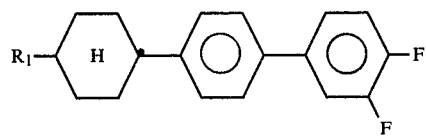

the 4-(trans-4-alkylcyclohexyl)-2',3'-difluoro-4'-($R_7$)-biphenyls of formula (Id),

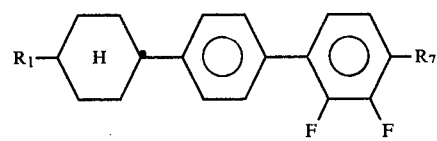

the 2,3-difluoro-4-(trans-4-alkylcyclohexyl)-4'-($R_7$)-biphenyls of formula (Ie)

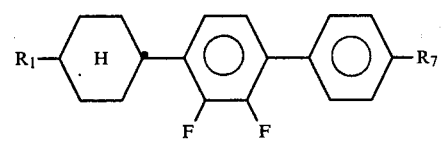

and the 2-fluoro-4-(trans-4-alkylcyclohexyl)-4'-($R_7$)-biphenyls of formula (If)

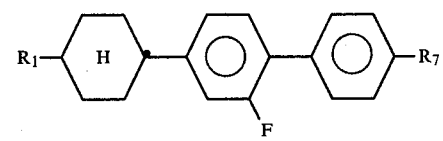

$R_7$ in these partial formulae is alkyl or alkoxy of 1–12 C atoms or CN, and $R_1$ is as defined for formula (I). The trans-position of the substituents in the 1-position and 4-position of the cyclohexane ring is marked in the formulae by a thickened black dot on the right-hand side of the ring. Those compounds of formula (I) which are not comprised by the formulae (Ia) to (If) admittedly have the same advantageous properties as those of these formulae, but they are more difficult to prepare and therefore less economical. The compounds of the formulae (Ia) to (If) are therefore preferred.

Among the compounds of formula (I), those of the partial formulae (Ia) to (Ic) have a positive dielectric anisotropy; by contrast, the compounds of the partial formulae (Id) to (If) have a negative dielectric anisotropy, or values of around zero, when $R_7$ is alkyl or alkoxy; and they have a diminished positive dielectric anisotropy, when $R_7$ in CN.

In the compounds of formula (I), the alkyl radical $R_1$ and the alkyl or alkoxy radical $R_6$ can be straightchain or branched. If the radical is straight-chain, i.e., it is methyl, ethyl, n-propyl, n-butyl, n-pentyl, n-hexyl, n-heptyl, n-octyl, n-nonyl, n-decyl, n-undecyl or n-dodecyl, the resultant compounds, as a rule, have higher clear points than the compounds with branched wing groups $R_1$ and/or $R_6$. For this reason, usually at most one of the wing groups $R_1$ and $R_6$ contains a branched carbon chain.

Compounds of formula (I) with a branched wing group $R_1$ or $R_6$ are occasionally important due to a higher solubility in the conventional liquid-crystalline base materials; but in particular they are important as chiral doping substances if they possess optical activity because of the chain branching. Such branched wing groups generally do not contain more than one chain branching. Those branched hydrocarbon radicals are preferred in which a metnhyl or ethyl group is present in the 1-position, 2-position or 3-position of a longer carbon chain, for example 2-methyl-propyl, 2-methylbutyl, 3-methylbutyl, 2-methylpentyl, 3-methylpentyl, 2-ethylhexyl or 1-methylhexyl. If $R_6$ is alkyl or alkoxy, the wing groups $R_1$ and $R_6$ together can contain up to 24 carbon atoms. In such cases, within the scope of the present invention, it is preferred that $R_1$ and $R_6$ together contain 3 to 14, in particular 4 up to 12, carbon atoms.

The compounds of this invention can be prepared by methods which are conventional for substances of this type. Thus, the 4-(trans-4-alkylcyclohexyl)-4'-fluorobiphenyls of formula (Ia) can be obtained by nitrating the known 4-(trans-4-alkylcyclohexyl)-biphenyls, unsubstituted in the 4'-position, to give the corresponding 4'-nitro compounds which are reduced to the 4'-amino compounds and converted, into the 4'-fluoro compounds in a manner which also is in itself known, according to Schiemann-Balz. For the preparation of the 3',4'-difluoro compounds of the formula (Ic), a 4-(trans-4-alkylcyclohexyl)-4'-aminobiphenyl is first acetylated and then nitrated to the 3+-nitro-4'-acetamidobiphenyl derivative which is then converted by reduction and hydrolysis into the 3',4'-diaminobiphenyl derivative. The 3',4'-difluorobiphenyl derivative is then obtained, in turn, from the latter by diazotization, reaction with fluoborate and thermal decomposition.

The compounds of formula (I), wherein $R_6$ is alkyl or alkoxy and one or two of the radicals $R_2$ to $R_5$ are fluorine, are prepared analogously from the correspondingly substituted mononitro or dinitro compounds. These starting materials are obtained by nitration of the 4-(trans-4-alkylcyclohexyl)-4'-(alkyl- or -alkoxy)-biphenyls. The distribution of isomers in the resulting mixture of nitration products can be directed in the direction of the main desired products by a suitable selection of the nitration conditions which are in themselves known from the literature, for example the nature and concentration of the nitrating agent, the solvent, the temperature, the duration of the reaction and/or the catalyst. The desired products can then be separated in conventional manner from the resulting mixtures of isomrs, for example by chromatographic methods. The reduction of the nitro compounds to the amino compounds is carried out by standard methods, for example by catalytic hydrogenation, by treatment with aqueous dithionite or with tin-II chloride and hydrochloric acid. The Schiemann-Balz synthesis is likewise carried out in a manner which is in itself known, for example according to one of the process variants described in "Organic Reactions", Volume 5 (1949), pages 193–228.

The dielectrics of this invention generally consist of 2 to 15, preferably 3 to 12, components which include at least one fluorine-containing cyclohexylbiphenyl derivative of formula (I). The other constituents are selected from among the nematic or nematogenic substances from the classes of azoxybenzenes, benzylidene-anilines, biphenyls, terphenyls, phenyl benzoates or cyclohexyl benzoates, cyclohexanecarboxylic acid phenyl or cyclohexyl esters, phenylcyclohexanes, cyclohexylbiphenyls, cyclohexylcyclohexanes, cyclohexylnaphthalenes, 1,4-bis-cyclohexylbenzenes, 4,4'-bis-cyclohexylbiphenyls, phenyl- or cyclohexyl-pyrimidines, phenyl- or cyclohexyldioxanes, optionally halogenated stilbenes, benzyl phenyl ethers, tolanes and substituted cinnamic acids. The most important compounds which can be used as constituents of liquid-crystalline dielectrics of this type can be characterized by formula (II).

$R_8$—Ⓐ—B—Ⓒ—$R_9$   (II)

wherein A and C each are a carbocyclic or heterocyclic ring system selected from the group comprising 1,4-disubstituted benzene rings and cyclohexane rings, 4,4'-disubstituted biphenyl, phenylcyclohexane and cyclohexylcyclohexane systems, 2,5-disubstituted pyrimidine rings and 1,3-dioxane rings, 2,6-disubstituted naphthalene, dihydro- and tetrahydro-naphthalene, quinazoline and tetrahydroquinazoline; B is

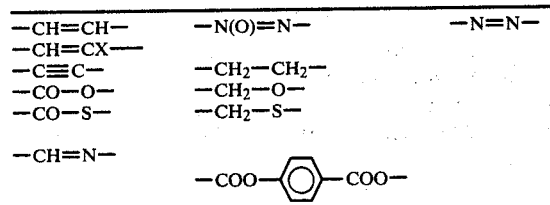

| —CH=CH— | —N(O)=N— | —N=N— |
| —CH=CX— | | |
| —C≡C— | —CH₂—CH₂— | |
| —CO—O— | —CH₂—O— | |
| —CO—S— | —CH₂—S— | |
| —CH=N— | | |
| | —COO—⬡—COO— | | or a C—C single bond; X is halogen, preferably chlorine, or —CN; and $R_8$ and $R_9$ are alkyl, alkoxy, alkanoyloxy or alkoxycarbonyloxy each of up to 18, preferably up to 8, carbon atoms, or one of these radicals can also be —CN, —NC, —NO₂, —CH₃, F, Cl or Br. In most of these compounds, $R_8$ and $R_9$ are different from one another, one of these radicals being an alkyl or alkoxy group in most cases. Other variants of the envisaged substituents, however, are also common. Many such substances, or mixtures thereof, are commercially available.

The dielectrics of this invention contain, as a rule, at least 30, preferably 50–99, in particular 60–98, percent by weight of the compounds of formula (I) and (II). Of this, preferably, at least 5 percent by weight, and in most cases even 10 or more percent by weight, is constituted by one or more compounds of formula (I). The invention also comprises those liquid-crystalline dielectrics to which only less than 5 percent by weight, for example 0.1 to 3 percent by weight, of one or more compounds of formula (I) have been added, for example for doping purposes. On the other hand, the compounds of formula (I) can account for up to 50 percent by weight of the dielectrics according to this invention. Preferably, the liquid-crystalline dielectrics of this invention contain 10 to 30 percent by weight of one or more compounds of formula (I).

The preparation of the dielectrics according to the invention is carried out in a manner conventional per se. As a rule, the desired quantity of the components used in a smaller quantity is dissolved in the component representing the main constituent, advantageously at elevated temperature. If a temperature above the clear point of the main constituent is chosen for this, the completeness of the solution process can be observed with ease.

It is also possible, however, to mix solutions of the components of formulae (I) and (II) in a suitable organic solvent, for example acetone, chloroform or methanol, and, after thorough mixing, to remove the solvent for example by distillation under reduced pressure. Of course, it is necessary in this procedure to take care that no impurities or undesired doping substances are introduced by the solvent.

The liquid-crystalline dielectrics of this invention can be modified by suitable additives in such a way that they can be used in all hitherto disclosed types of liquid crystal display elements. Additives of this type are known to those skilled in the art and are extensively described in the relevant literature. For example, it is possible to add dichroic dyestuffs or substances which modify the dielectric anisotropy the viscosity, the conductivity and/or the orientation of the nematic phases. Substances of this type are described, for example, in German Offenlegungsschriften Nos. 2,209,127, 2,240,864, 2,321,632, 2,338,281, 2,450,088, 2,637,430, 2,853,728 and 2,902,177, whose disclosures are incorporated by reference herein.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

In the examples, m.p. denotes the melting point, and c.p. denotes the clear point, of a liquid-crystalline substance in degrees centigrade; boiling points are marked b.p.

EXAMPLE 1

(a) 15.3 g of 4-(trans-4-n-pentylcyclohexyl)biphenyl is introduced in portions into a warm mixture, at 40°, of 5 ml of 65% nitric acid and 6 ml of 96% sulfuric acid. After the end of the addition, the reaction mixture is stirred for 1 further hour at 60° and is poured onto 150 g of ice. After thawing, the 4-(trans-4-n-pentylcyclohexyl)-4'-nitrobiphenyl which has crystallized out is filtered off and recrystallized from ethanol; m.p. 115°, c.p. 176°.

(b) Under normal pressure and at room temperature, hydrogen is passed for one hour into a suspension of 3 g of palladium-on-carbon (10% of Pd) in a solution of 10 g of 4-(trans-4-n-pentylcyclohexyl)-4'-nitrobiphenyl in 100 ml of tetrahydrofuran. The catalyst is then filtered off and the filtrate is evaporated. The remaining 4-(trans-4-n-pentylcyclohexyl)-4'-aminobiphenyl is recrystallized from petroleum ether (boiling range 40°–60°); m.p. 132°, c.p. 215°.

(c) 7.8 g of 4-(trans-4-n-pentylcyclohexyl)-4'-aminobiphenyl is suspended in 5 ml of 36% aqueous hydrochloric acid.

After the addition of 5 ml of dioxane, the solution of 1.9 g of sodium nitrite in 7.5 ml of water is added dropwise at 0°. Immediately afterwards, and likewise at 0°, a solution of 6 g of sodium tetrafluoborate in 10 ml of water is added dropwise. The precipitate which forms is filtered off ½ hour after the end of the addition of the fluorine compound, washed with ice water and dried in vacuo at room temperature. The dried powder is heated to 120°. When the evolution of $BF_3$ has ceased, the residue is dissolved in ethanol. 3.5 g of 4-(trans-4-n-pentylcyclohexyl)-4'-fluorobiphenyl of m.p. 99° and c.p. 154° crystallizes from the solution.

The following are prepared analogously:
4-(trans-4-methylcyclohexyl)-4'-fluorobiphenyl,
4-(trans-4-ethylcyclohexyl)-4'-fluorobiphenyl,
4-(trans-4-n-propylcyclohexyl)-4'-fluorobiphenyl,
4-(trans-4-n-butylcyclohexyl)-4'-fluorobiphenyl,
4-(trans-4-n-hexylcyclohexyl)-4'-fluorobiphenyl,
4-(trans-4-n-heptylcyclohexyl)-4'-fluorobiphenyl,
4-(trans-4-n-decylcyclohexyl)-4'-fluorobiphenyl,
4-(trans-4-n-dodecylcyclohexyl)-4'-fluorobiphenyl and
4-[trans-4-(2-methylbutyl)-cyclohexyl]-4'-fluorobiphenyl.

EXAMPLE 2

(a) 16.7 g of 4-(trans-4-n-pentylcyclohexyl)-4'-ethylbiphenyl is nitrated in the manner described in Example 1(a). The mixture of isomeric nitration products is poured into ice water, filtered off and then dissolved in toluene and is then separated by high-pressure liquid chromatography on a preparative scale. This gives 8.7 g of 4-(trans-4-n-pentylcyclohexyl)-2'-nitro-4'-ethylbiphenyl and 5.5 g of 4-(trans-4-n-pentylcyclohexyl)-2-nitro-4'-ethylbiphenyl.

(b) The nitro compounds prepared according to Example 2(a) are reduced, analogously to Example 1(b), to the corresponding amino compounds and the latter are converted analogously to Example 1(c) into 4-(trans-4-n-pentylcyclohexyl)-2'-fluoro-4'-ethylbiphenyl, m.p. 27°, c.p. 104° and 4-(trans-4-n-pentylcyclohexyl)-2-fluoro-4'-ethylbiphenyl, m.p. 26°, c.p. 107°.

The following are prepared analogously:
4-(trans-4-ethylcyclohexyl)-2'-fluoro-4'-n-butylbiphenyl,
4-(trans-4-n-propylcyclohexyl)-2'-fluoro-4'-n-propylbiphenyl,
4-(trans-4-n-propylcyclohexyl)-2'-fluoro-4'-n-octylbiphenyl,
4-(trans-4-n-butylcyclohexyl)-2'-fluoro-4'-n-butylbiphenyl,
4-(trans-4-n-pentylcyclohexyl)-2'-fluoro-4'-n-propylbiphenyl,
4-(trans-4-n-pentylcyclohexyl)-2'-fluoro-4'-n-pentylbiphenyl, smectic-nematic phase transition at 52°, c.p. 105°;
4-(trans-4-n-heptylcyclohexyl)-2'-fluoro-4'-n-butylbiphenyl,
4-(trans-4-n-octylcyclohexyl)-2'-fluoro-4'-methylbiphenyl,
4-(trans-4-ethylcyclohexyl)-2-fluoro-4'-n-butylbiphenyl,
4-(trans-4-n-propylcyclohexyl)-2-fluoro-4'-n-propylbiphenyl,
4-(trans-4-n-propylcyclohexyl)-2-fluoro-4'-n-octylbiphenyl,
4-(trans-4-n-butylcyclohexyl)-2-fluoro-4'-n-butylbiphenyl,
4-(trans-4-n-pentylcyclohexyl)-2-fluoro-4'-n-propylbiphenyl,
4-(trans-4-n-pentylcyclohexyl)-2-fluoro-4'-n-pentylbiphenyl,
4-(trans-4-n-heptylcyclohexyl)-2-fluoro-4'-n-butylbiphenyl,
4-(trans-4-n-octylcyclohexyl)-2-fluoro-4'-methylbiphenyl and
4-(trans-4-n-pentylcyclohexyl)-2,2'-difluoro-4'-ethylbiphenyl, m.p. −2°, c.p. 80°.

The following examples relate to liquid-crystalline dielectrics according to this invention:

EXAMPLE A

The liquid crystalline dielectric composed of
24% of 4-(trans-4-n-propylcyclohexyl)-benzonitrile,
36% of 4-(trans-4-n-pentylcyclohexyl)-benzonitrile,
25% of 4-(trans-4-n-heptylcyclohexyl)-benzonitrile and
15% of 4-(trans-4-n-pentylcyclohexyl)-biphenyl-4'-carbonitrile has a nematic range from −6° to +70° and a viscosity of $28 \times 10^{-3}$ Pa.s at 20° and $97 \times 10^{-3}$ Pa.s at 0°. If the last-mentioned component in this mixture is replaced by the same quantity by weight of 4-(trans-4-n-pentylcyclohexyl)-4'-fluorobiphenyl, the temperature range of the nematic phase changes slightly to a range from −10° to +65°; the viscosity values, which have a significant influence on the switching times, in the dielectric according to this invention, thus prepared, are $24 \times 10^{-3}$ Pa.s at 20° and only $68 \times 10^{-3}$ Pa.s at 0°.

EXAMPLE B

The liquid crystalline dielectric composed of
12% of 4-n-propylphenyl anisate,
23% of 4-n-pentylphenyl anisate,
9% of 1-[4-(trans-4-n-pentylcyclohexyl)-phenyl]-pentan-1,3-dion,
21% of 4-(trans-4-n-propylcyclohexyl)-benzoic acid 4-n-butyl-2-cyanophenyl ester and
35% of 4-(trans-4-n-pentylcyclohexyl)-2'-fluoro-4'-ethylbiphenyl has a nematic range from −11° to +78°, a viscosity of $65 \times 10^{-3}$ Pa.s at 20° and a dielectric anisotropy $\Delta\epsilon$ of −0.6. It is well suited for liquid crystal displays based on the dynamic scattering effect.

EXAMPLE C

The liquid crystalline dielectric composed of
23% of 4-n-pentylphenyl anisate,
11% of 1-[4-(trans-4-n-pentylcyclohexyl)-phenyl]-pentan-1,3-dion,
21% of 4-(trans-4-n-propylcyclohexyl)-benzoic acid 4-n-butyl-2-cyanophenyl esters,
15% of 4-(trans-4-n-pentylcyclohexyl)-4'-ethylbiphenyl and
30% of 2-fluoro-4-(trans-4-n-pentylcyclohexyl)-4'-ethylbiphenyl has a nematic range from −13° to +94°, a viscosity of $69 \times 10^{-3}$ Pa.s at 20° and of $298 \times 10^{-3}$ Pa.s at 0°. The dielectric anisotropy $\Delta\epsilon$ is −0.5. This dielectric is most suitable for dynamic scattering liquid crystal displays which are operable in a broad temperature range.

EXAMPLE D

The liquid crystalline dielectric composed of
17% of 4-(trans-4-n-propylcyclohexyl)-benzonitrile,
12% of 4-(trans-4-n-butylcyclohexyl)-benzonitrile,
13% of 4-(trans-4-n-pentylcyclohexyl)-benzonitrile,
15% of 4-(trans-4-n-propylcyclohexyl)-ethylbenzene,
21% of 4-(trans-4-n-pentylcyclohexyl)-4'-ethylbiphenyl,
12% of 4-(trans-4-n-pentylcyclohexyl)-4'-(trans-4-n-propylcyclohexyl)-biphenyl,
5% of 4-(trans-4-n-pentylcyclohexyl)-4'-cyanobiphenyl, and
5% of 4-(trans-4-n-pentylcyclohexyl)-4'-fluorobiphenyl
has a nematic range from $-11°$ to $+92°$, a viscosity of $20 \times 10^{-3}$ Pa.s at $20°$, of $61 \times 10^{-3}$ Pa.s at $0°$, and of $316 \times 10^{-3}$ Pa.s at $-20°$ in the supercolled melt. The dielectric anisotropy $\Delta\epsilon$ is $+5.4$. This dielectric can advantageously be used in twisted nematic cell liquid crystal displays which are exposed to large temperature variations.

EXAMPLE E

The liquid crystalline dielectric composed of
17% of 4-(trans-4-n-propylcyclohexyl)-benzonitrile,
12% of 4-(trans-4-n-butylcyclohexyl)-benzonitrile,
18% of 4-(trans-4-n-pentylcyclohexyl)-benzonitrile,
15% of 4-(trans-4-n-propylcyclohexyl)-n-butylbenzene,
21% of 4-(trans-4-n-pentylcyclohexyl)-4'-ethylbiphenyl,
12% of 4-(trans-4-n-pentylcyclohexyl)-4'-(trans-4-n-propylcyclohexyl)-biphenyl and
5% of 4-(trans-4-n-propylcyclohexyl)-4'-fluorobiphenyl
has a nematic range from $-11°$ to $+84°$, a viscosity of $19 \times 10^{-3}$ Pa.s at $20°$, of $56 \times 10^{-3}$ Pa.s at $0°$ and of $290 \times 10^{-3}$ Pa.s at $-20°$ in the supercooled melt. The threshold voltage at use of this dielectric in the twisted nematic cell is 2.0 Volts at $20°$.

EXAMPLE F

The liquid crystalline dielectric composed of
10% of 4-(trans-4-n-propylcyclohexyl)-benzonitrile,
10% of 4-(trans-4-n-propylcyclohexyl)-phenetole,
22% of 4-(trans-4-n-propylcyclohexyl)-ethylbenzene,
15% of 4-(trans-4-n-pentylcyclohexyl)-4'-ethylbiphenyl,
9% of 4-(trans-4-n-pentylcyclohexyl)-4'-(trans-4-n-propylcyclohexyl)-biphenyl,
8% of trans-4-n-pentylcyclohexyl carboxylic acid 4-(trans-4-n-propylcyclohexyl)-phenyl ester,
8% of 4-(trans-4-n-propylcyclohexyl)-4'-ethylbiphenyl and
18% of 4-(trans-4-n-propylcyclohexyl)-2'-fluoro-4'-ethylbiphenyl
has a nematic range from $-17°$ to $+86°$, a viscosity of $18 \times 10^{-3}$ Pa.s at $20°$, of $47 \times 10^{-3}$ Pa.s at $0°$ and of $225 \times 10^{-3}$ Pa.s at $-20°$ in the supercooled melt. The threshold voltage in the twisted nematic cell is 2.8 Volts at $20°$.

The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope thereof, can make various changes and modifications of the invention to adapt it to various usages and conditions.

We claim:

1. A cyclohexylbiphenyl of the formula

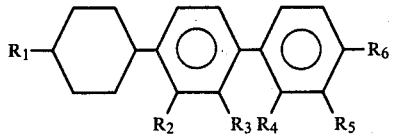

wherein $R_1$ is alkyl of 1-12 C atoms; $R_6$ is alkyl or alkoxy each of 1-12 C atoms, CN or fluorine; and $R_2$, $R_3$, $R_4$ and $R_5$ each is hydrogen or fluorine, with the proviso that at least one of $R_4$ and $R_5$ is fluorine, but not more than two of $R_2$, $R_3$, $R_4$, $R_5$ and $R_6$ are fluorine.

2. A compound of claim 1 of the formula

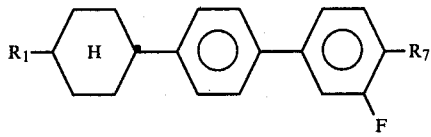

wherein $R_1$ is alkyl of 1-12 C atoms and $R_7$ is alkyl or alkoxy of 1-12 C atoms or CN.

3. A compound of claim 1 of the formula

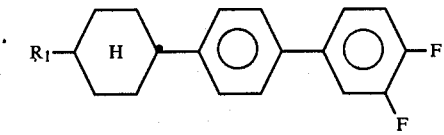

wherein $R_1$ is alkyl of 1-12 C atoms.

4. A compound of claim 1 of the formula

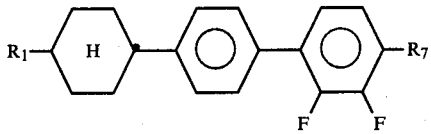

wherein $R_1$ is alkyl of 1-12 C atoms and $R_7$ is alkyl or alkoxy of 1-12 C atoms or CN.

5. A liquid-crystalline dielectric comprising two or more liquid-crystalline components, wherein at least one component is a cyclohexylbiphenyl of claim 1.

6. A liquid-crystalline dielectric of claim 5 wherein the amount of the cyclohexylbiphenyl is up to 50 wt. percent.

7. An electro-optical display element having a liquid crystal cell comprising a liquid-crystalline dielectric of claim 5.

8. A compound of claim 1 wherein $R_2$ and $R_3$ are each hydrogen.

* * * * *